United States Patent
Kirschner et al.

(10) Patent No.: US 6,635,456 B2
(45) Date of Patent: Oct. 21, 2003

(54) PROCEDURE FOR THE PREPARATION OF PURE PHOSPHATIDES WITH PHOSPHOLIPASE D

(75) Inventors: Guenter Kirschner, Abano Terme (IT); Giampaolo Menon, Battaglia Terme (IT); Susanna Vaccaro, Siracusa (IT)

(73) Assignee: Fidia Farmaceutici S.p.A., Abano Terme (IT)

(*) Notice: Subject to any disclaimer, the term of this patent is extended or adjusted under 35 U.S.C. 154(b) by 0 days.

(21) Appl. No.: 09/925,000

(22) Filed: Aug. 8, 2001

(65) Prior Publication Data

US 2002/0155558 A1 Oct. 24, 2002

(30) Foreign Application Priority Data

Feb. 9, 2001 (IT) ..................... PA2001A0031

(51) Int. Cl.$^7$ .................... C12P 7/64
(52) U.S. Cl. ............ 435/134; 435/132; 435/128; 435/198; 435/197; 435/168; 424/94.6
(58) Field of Search ................. 435/132, 128, 435/168, 134, 198, 197; 424/94.6

(56) References Cited

U.S. PATENT DOCUMENTS

| 4,699,879 | A | | 10/1987 | Umezawa et al. |
|---|---|---|---|---|
| 5,466,595 | A | * | 11/1995 | Jones et al. ............... 435/198 |
| 5,700,668 | A | | 12/1997 | De Ferra et al. |
| 5,900,409 | A | | 5/1999 | Sakai et al. |
| 6,117,853 | A | | 9/2000 | Sakai et al. |

FOREIGN PATENT DOCUMENTS

| DE | 199 17 249 A1 | 9/2000 |
|---|---|---|
| EP | 0711559 | 5/1996 |
| EP | 0 776 976 A2 | 6/1997 |
| EP | 0 7760976 A3 | 9/1997 |
| EP | 0922707 | 6/1999 |
| EP | 1 048 738 A1 | 11/2000 |
| EP | 0776976 | 11/2001 |
| JP | 0542917 | 6/1993 |

OTHER PUBLICATIONS

ATCC Catalogue of Bacteria, p. 405, 1996.*
Nakajima et al., Biotechnol. Bioeng. (1994), 44(10), 1193–8.*

* cited by examiner

*Primary Examiner*—Irene Marx
(74) *Attorney, Agent, or Firm*—Birch, Stewart, Kolasch & Birch, LLP

(57) ABSTRACT

Process for preparing pure phosphatides starting from mixtures of natural phosphatides, or their single components, such as soybean or egg lecithin or animal phospholipids, or from synthetic phosphatides by reacting them both with phospholipase D derived from *Streptomyces hachijoense* in a completely aqueous medium in the presence of defined substates containing a primary or secondary alcoholic group, and their uses thereof.

10 Claims, No Drawings

PROCEDURE FOR THE PREPARATION OF PURE PHOSPHATIDES WITH PHOSPHOLIPASE D

SUBJECT OF THE INVENTION

The present invention concerns a process for the preparation of pure phosphatides starting from mixtures of natural phosphatides, or their single components, such as soybean or egg lecithin or animal phospholipids, or from synthetic phosphatides by reacting them with phospholipase D, with transphosphatidylation activity, in aqueous medium alone in the presence of defined substrates containing a primary or a secondary alcoholic group. The invention also refers to the preparation, purification and characterisation of the phospholipase D used in the process.

BACKGROUND OF THE INVENTION

The synthesis of pure phospholipids, particularly on an industrial scale, is a particularly widespread problem. Indeed, there have been numerous scientific publications and patents, including some very recent ones that describe various methodologies. Generally, said methods exploit the transphosphatidylation properties of phospholipase D to obtain optically active phosphatides. One of the main problems is the fact that each of these methods is suited to the preparation of one specific phosphatide alone and cannot be adapted for the synthesis of the whole class of compounds. Generally, the most widely studied phospholipid is phosphatidylserine (PS), as it is widely used in the preparation of pharmaceutical compositions, in the preparation of liposome formulations and food supplements. Relatively little or nothing is reported concerning the synthesis of sphingophospholipids.

One limitation of all the methods reported in both the scientific and patent literature consists in the fact that the reaction of transphosphatidylation occurs in diphasic water/organic solvent systems. This presents a series of technical problems linked with the use of large quantities of solvent, especially when the industrial process is of a chemical nature, aimed at obtaining a quality product. In patent application No. DE 19917249 A1, a method is described that actually employs the aqueous phase alone, but neither the yield nor degree of purity of the PS obtained, nor the type of the utilised enzyme is reported. Moreover, there is no mention of whether it is possible to obtain other phospholipids besides PS by using the same technique and starting from the substrates used, or whether in the conditions described other phospholipids can act as reaction substrate. Japanese Patent Publication No. 5/42917 (JP 2130088) also discloses a method employing a medium comprised of water alone or a mixture of water and an organic solvent. However, this patent states that the water content is favored to be 10% by weight or less to prevent a side reaction. This reference, therefore, appears to suggest that using an aqueous environment alone is not favorable. In fact, the examples therein disclose only processes employing a biphasic mixture of water and ethyl ether.

The generic nature of the information given or absence of teaching in the aforesaid prior art concerning the applicability of the transphosphatidylation reaction of phospholipase D in aqueous phase alone could in no way have led an expert in the field to think that this was the solution to the problem. Moreover, the importance of removing impurities deriving from the use of organic solvents in processes for the manufacture of products for use in the alimentary and pharmaceutical fields has only become known in recent years, following the limitations dictated by the United States Pharmacopoeia (USP) and the European guidelines (CPMP/CH/283/95).

Another critical point that has not been investigated in-depth, either in the scientific literature or in patents, concerns the peroxidation of products caused by the use of heterogeneous phases of water/solvent in emulsion during the transphosphatidylation reaction, the reaction conditions used and the consequent need to perform numerous steps of the process (re-precipitation, washings and possibly also chromatography) to obtain products with a high degree of purity. Many of the solvents used for these reactions in the heterogeneous phase do not guarantee the absence of radicalic precursors typical of the initiation of the peroxidation reaction. Moreover, the shaking/stirring required to achieve a reaction in the heterogeneous phase increases the likelihood of there being contact with oxygen in the atmosphere and consequent triggering of oxidative phenomena. This peroxidation acts like a chain reaction, when even negligible initial primer steps can give devastating results over time, even though the triggering conditions have been eliminated or minimised. The peroxidation of a "fatty" substance such as triglycerides (oils or fats) and phospholipids too, causes the fatty acids to become "rancid", with the consequent formation of an unpleasant smell and taste. It is particularly important that the products should have a high degree of palatability (smell and taste) when they, particularly PS, are used to prepare food supplements (nutraceuticals) with particular formulations such as granules or the so-called "functional foods", to which the product is added to enrich their content. Consequently, it is important that the products obtained, particularly PS, should be clearly characterised in chemical terms, both with regard to the chemical composition of the fatty acids, and for the extent of their peroxidation and consequent palatability.

Lastly, it should be pointed out that the phospholipase D enzymes available on the market mainly have transphosphatidylation activity on the phosphatidylcholine fraction of the phospholipid mixture. Therefore, the other components such as phosphatidylethanolamine (PE) undergo hydrolysis to phosphatidic acid, thus reducing both the yield and the degree of purity of the finished product.

DETAILED DESCRIPTION OF THE INVENTION

Surprisingly, the Applicant has discovered that by using a purified fraction of phospholipase D from *Streptoverticillium hachijoense* (n/k/a *Streptomyces hachijoense*) it is possible to obtain a transphosphatidylation reaction with various alcoholic receptors starting from a mixture of natural phosphatides or their purified fractions in a 100% aqueous environment with high yields of product, a high degree of purity and a peroxide index (degree of peroxidation) of less than 5, established according to the European Pharmacopoeia—Suppl 2000, page 41 (method A), by one single reaction step and one single precipitation.

A second aspect of the present invention consists in the fact that this particular enzymatic preparation has a transphosphatidylation activity with high yields even on substrates other than phosphatidylcholine (lecithin), thus enabling the process to be used with low-cost, unpurified raw materials too.

The importance of the strain used for the preparation of the Phospholipase D and its fractionation can be deduced from the following table, where a comparison with different commercial enzymatic preparations is reported for the purified enzymatic fraction prepared according to Example 1.

| Preparation of phosphaditylserine | | | | | |
|---|---|---|---|---|---|
| Strain | Company | Product | PS | PA | PC |
| Streptomyces sp. | Sigma | P4912 type VI | 50% | 45% | 5% |
| Streptomyces sp. | Asahi Chemical Industry Co., Ltd | PL-DP | 50% | 45% | 5% |
| Streptomyces chromofuscus | Sigma | P8023 type VI | 40% | 40% | 20% |
| Actinomadura sp. | Meito Sangyo Co., Ltd | No code | 45% | 40% | 15% |
| Streptoverticillium hachijoense | Fidia | FRS | 95% | 5% | — | pure lecithin, phosphatidylcholine content 95%, as substrate; reaction conditions as in example 1

Another advantage of the actual enzyme preparation and of the reaction conditions described in the instant invention is the practically complete conversion of the substrate to PS as compared to the conversion rate of not more than 70% achieved in JP 213008's diphasic water/organic solvent system.

A third aspect of the present invention concerns the preparation of pharmaceutical and cosmetic compositions and food and dietary supplements based on phospholipids, obtained according to the process described above, having a degree of peroxidation of less than 5 and a high degree of palatability, such as to make them preferable to other, similar products on the market that do not however have the above said characteristics.

The pharmaceutical compositions and the food and dietary supplements are particularly indicated in the treatment of conditions of psycho-physical stress with attention, concentration and memory deficits, often associated with advancing age, and they can be prepared, for example, in the form of capsules, tablets and granules.

The cosmetic compositions can chiefly be applied in the treatment of skin with impaired physiological functions and as aids in the therapy of dermatitis of an eczematous and/or inflammatory type, and they can be prepared, for example, in the form of creams or gels.

For purely illustrative purposes, we report hereafter some preparation examples of Phospholipase D and phospholipids derived from it according to the present invention

EXAMPLE 1

Preparation of Phospholipase D

The *Streptoverticillium hachijoense* ATCC 19769 strain is used.

Preparation of the inoculation to be used in the fermentation test begins with a colony on solid medium in a Petri dish. The composition of the solid medium is as follows: 21.0 g/liter Y.M., 2% agar. The bacteria taken from the Petri dishes are used to start a "scale-up" system in Ehrlenmeyer flasks as follows:
- the bacteria are taken from the solid medium with a sterile platinum loop and inoculated in a 100-ml flask containing 20 ml of medium with the following composition: 21.0 g/lt of Y. M. broth;
- the flask is placed in a shaker incubator set at 30° C., 150 rpm for 48 hours;
- 20 ml of culture is transferred to a 5.0-lt flask containing 2.5 lt of medium with the composition described above;
- the flask is placed in a shaker incubator set at 30° C., 150 rpm for 72 hours.

At this point the culture is ready to be inoculated in the fermenter. This operation is made possible by the fact that the culture is in a flask fitted with a silicone tube and needle system. The fermenter used has a capacity of 50 lt (Braun Biostat U). The composition of the medium is as follows: Y.M. broth 21.0 gr/lt, pH 6.5 (the medium is sterilised directly in the fermenter by the addition of an antifoaming agent); the parameters of fermentation are: shaking at 200 rpm, temperature 30° C., air flow 0.5 vvm.

After 72 hours fermentation is interrupted. The maximum amount of enzyme reached is 5,000 U/lt and enzymatic activity is determined by the modified method of Kato et al. described in the literature (K. Shimbo et al., Agric. Biol. Chem. 54(5), 1189-93, 1990).

The culture broth is filtered to eliminate the biomass, the supernatant is concentrated using a spiral cartridge in cellulose acetate with a molecular cut-off of 10,000 D, and dialised against 50 mM Tris-HCl buffer, pH 8.0. The sample thus obtained is loaded on a chromatographic column (i.d.= 10 cm, h=50 cm) packed with 500 gr of Whatman DE-52 anion-exchange resin pre-balanced with the same buffer as was used for dialysis. The enzyme is not adsorbed and elutes from the column, it is dialised against 20 mM Na-phosphate buffer, pH 5.4 and is then loaded on a chromatographic column (i.d.=10 cm, h=50 cm) packed with 50 gr of cationic exchange resin CM-Sephadex Pharmacia C-50 pre-balanced with the same buffer as the enzyme. The enzyme is eluted with a pH gradient of between 5.4 and 7.0 using an Na-phosphate buffer, 20 mM, pH7.0. The fraction that elutes at pH 6.2 is harvested, concentrated and dialised against Tris-HCl buffer, 50 mM, pH 8.0, to a concentration of 100 U/ml and then freeze-dried.

| | Total activity (Unit × $10^3$) | Total proteins (mg × $10^3$) | Specific activity (Unit × $mg_{prot}$) | Recovery (%) |
|---|---|---|---|---|
| Crude broth | 250 | 250 | 1 | 100 |
| Concentration and dialysis | 237.5 | 118.8 | 2 | 95 |
| DE-52 Whatman | 212.5 | 2.2 | 97 | 85 |
| CM-Sephadex C-50 Pharmacia | 150 | 0.26 | 577 | 60 |
| Concentration and dialysis | 145 | 0.24 | 604 | 58 |
| Freeze-drying | 112.5 | 0.24 | 469 | 45 |

EXAMPLE 2

Preparation of PS from PC

In a jacketed reactor fitted with a shaker and reflux condenser, 272 g of sodium acetate trihydrate and 59 gr of calcium hydrochloride trihydrate are dissolved in 10 lt of water. The pH is adjusted to 5.6 (acetate buffer, 0.2 M+calcium chloride, 0.04 M, pH 5.6) and 5.0 kg of L-serine is added and solubilised by heating to 45° C. The entire process is conducted under nitrogen.

Once solubilisation is complete, 1.5 kg of purified soybean lecithin with the following composition is added: PC 95%, PA 4%, lyso-PC 1%. Ten minutes later, 16,100 U of phopholipase D as in example 1 are added, and this is left to react for 24 hours at 45° C.

On completion of the reaction, the reactor is unloaded by adding 10 lt of a mixture of n-hexane/ispropanol/water (60/80/15); the mass is dissolved by shaking, then the shaking is stopped and the two phases are left to separate.

The lower phase is harvested and the unreacted L-serine is recovered by cooling in a crystallizer.

The upper phase is washed with 6,950 ml of HCl, 1 N and 1,113 ml of isopropanol at 5° C. The acid phase is counter-extracted with 10 lt of a mixture of hexane/isopropanol/water (60/80/15), after which the two organic phases are cascade-washed with a mixture of 7 lt of water and 6 lt of isopropanol.

The organic phases are concentrated under vacuum and precipitated by slowly adding a solution of 450 ml of sodium acetate, 4.5 M, in water in 33.2 lt of ethanol.

This is filtered and dried.

1.14 kg of phosphatidylserine with a titer of over 95%, a phosphatidic acid content of less than 5% and a peroxide index of less than 5 is obtained.

After crystallisation and drying, 3.25 kg of L-serine is harvested.

EXAMPLE 3

Preparation of PS from Egg Lecithin 180 ml of acetate buffer, 0.2 M+calcium chloride, 0.04 M, pH 5.6, are placed n a jacketed reactor with a shaker and reflux condenser, after which 90 gr of L-serine is added and solubilised by heating to 45° C. The entire process is conducted under nitrogen.

Once solubilisation is complete, 27 gr of purified egg lecithin is added (PC content≧95%); 10 minutes later, 290 U of phospholipase D as per example 1 is added and it is left to react for 24 hours at 45° C.

Once the reaction is complete, the reactor is unloaded by adding 200 ml of a mixture of n-hexane/isopropanol/water (60/80/15) and the mass is dissolved by shaking, then the shaking is stopped and the two phases are left to separate.

The lower phase is discarded.

The upper phase is washed with 150 ml of 1 N HCl and 30 ml of isopropanol at 5° C.

The acid phase is counterextracted with 180 ml of a mixture of n-hexane/isopropanol/water (60/80/15), then the two organic phases are washed in a cascade with a mixture of 100 ml water and 130 ml of isopropanol The organic phases are concentrated under vacuum and precipitated by the slow addition of a solution of 8 ml of 4.5 M sodium acetate in water in 600 ml of ethanol.

It is filtered and dried.

This yields 20.8 g of phosphatidylserine with a titer of over 95% with a phosphatidic acid content of less than 5% and a peroxide index of less than 5.

EXAMPLE 4

Preparation of Phosphatidylserine from Crude Soybean Lecithin 180 ml of acetate buffer, 0.2 M+calcium chloride, 0.04 M, pH 5.6 are placed in a jacketed reactor with a shaker and reflux condenser, after which 90 g of L-serine is added and solubilised by heating to 45° C. The entire process is conducted under nitrogen.

Once solubilisation is complete, 27 g of crude soybean lecithin is added (total phospholipid content 75%, percentage composition PC 60.6/PE 29.5/PA 3.4/lyso-PC 2.5/other 3.9)); 10 minutes later, 290 U of phospholipase D as per example 1 is added and this is left to react for 24 hours at 45° C.

Once the reaction is complete, the solution is unloaded by adding 200 ml of a mixture of n-hexane/isopropanol/water (60/80/15) into the reactor and the mass is dissolved by shaking, then the shaking is stopped and the two phases are left to separate.

The lower phase is discarded.

The upper phase is washed with 150 ml of 1 N HCl and 30 ml of isopropanol at 5° C.

The acid phase is counter-extracted with 180 ml of a mixture of n-hexane/isopropanol/water (60/80/15), then the two organic phases are washed in a cascade with a mixture of 100 ml water and 130 ml of isopropanol The organic phases are concentrated under vacuum and precipitated by the slow addition of a solution of 8 ml of 4.5 M sodium acetate in water in 600 ml of ethanol.

It is filtered and dried.

This yields 19 g of phosphatidylserine with a titer of 83.5% (PA 7.7%, lyso-PS 2.3%, PE 1.9%, other 4.5%) and a peroxide index of less than 5.

EXAMPLE 5

Preparation of Phosphatidyl-D-Serine 180 ml of acetate buffer, 0.2 M+calcium chloride, 0.04 M, pH 5.6 are placed in a jacketed reactor with a shaker and reflux condenser, after which 90 g of D-serine is added and solubilised by heating to 45° C. The entire process is conducted under nitrogen.

Once solubilisation is complete, 27 g of purified soybean lecithin as per example 2 is added; 10 minutes later, 290 U of phospholipase D as per example 1 is added and it is left to react for 24 hours at 45° C.

Once the reaction is complete, the reactor is unloaded by adding 200 ml of a mixture of n-hexane/isopropanol/water (60/80/15). The mass is dissolved by shaking, then the shaking is stopped and the two phases are left to separate.

The lower phase is discarded.

The upper phase is washed with 150 ml of 1 N HCl and 30 ml of isopropanol at 5° C.

The acid phase is counter-extracted with 180 ml of a mixture of n-hexane/isopropanol/water (60/80/15), then the two organic phases are washed in a cascade with a mixture of 100 ml water and 130 ml of isopropanol The organic phases are concentrated under vacuum and precipitated by the slow addition of a solution of 8 ml of 4.5 M sodium acetate in water in 600 ml of ethanol.

It is filtered and dried.

This yields 18.7 g of phosphatidyl-D-serine with a titer of over 95% with a phosphatidic acid content of less than 5% and a peroxide index of less than 5.

EXAMPLE 6

Preparation of Phosphatidylethanolamine (PE) from PC 200 ml of acetate buffer, 0.2 M+calcium chloride, 0.04 M, pH 5.6 are placed in a jacketed reactor with a shaker and reflux condenser. The entire process is conducted under nitrogen.

58 g of ethanolamine is added and the pH is adjusted to 5.6 with glacial acetic acid at a temperature setting of 30° C.

At the end of the operation, it is heated to 45° C. and 30 g of purified soybean lecithin as per example 2 is added.

After 10 minutes, 325 U of phospholipase D as per example 1 is added and this is left to react for 24 hours at 45° C.

Once the reaction is complete, the reactor is unloaded by adding 400 ml of a mixture of n-hexane/isopropanol/water (60/80/15), then the shaking is stopped and the two phases are left to separate.

The lower phase is discarded.

The upper phase is washed with 150 ml of 1 N HCl and 30 ml of isopropanol at 5° C.

The acid phase is counter-extracted with 180 ml of a mixture of n-hexane/isopropanol/water (60/80/15), then the two organic phases are washed in a cascade with a mixture of 100 ml water and 130 ml of isopropanol, then with 100 ml of sodium acetate, 1 N, and 130 ml of isopropanol.

The organic phases are concentrated under vacuum.

It is purified by silica gel chromatography using an axial pressure chromatograph with a 1 lt column equilibrated with chloroform/methanol (80/20); gradient elution is performed till chloroform/methanol/water (70/30/3).

The pure fractions are evaporated, dissolved in 250 ml of cyclohexane and freeze-dried, giving 24 g of a pale yellow, solid product, free from phosphatidic acid and lysoderivatives, and over 99% pure.

EXAMPLE 7

Preparation of Phosphatidyl-Homoserine from PC 180 ml of acetate buffer, 0.2 M+calcium chloride, 0.04 M, pH 5.6 are placed in a jacketed reactor with a shaker and reflux condenser, after which 102 g of homoserine is added and solubilised by heating to 45° C. The entire process is conducted under nitrogen.

Once solubilisation is complete, 27 g of purified soybean lecithin as per example 2 is added; 10 minutes later, 290 U of phospholipase D as per example 1 is added and it is left to react for 24 hours at 45° C.

Once the reaction is complete, the reactor is unloaded by adding 200 ml of a mixture of n-hexane/isopropanol/water (60/80/15). The mass is dissolved by shaking, then the shaking is stopped and the two phases are left to separate.

The lower phase is discarded.

The upper phase is washed with 150 ml of 1 N HCl and 30 ml of isopropanol at 5° C.

The acid phase is counter-extracted with 180 ml of a mixture of n-hexane/isopropanol/water (60/80/15), then the two organic phases are washed in a cascade with a mixture of 100 ml water and 130 ml of isopropanol The organic phases are concentrated under vacuum and precipitated by the slow addition of a solution of 8 ml of 4.5 M sodium acetate in water in 600 ml of ethanol.

This is filtered and dried.

22.6 g of phosphatidyl-homoserine is obtained, with a titer of over 95%, a phosphatidic acid content of less than 5% and a peroxide index of less than 5.

EXAMPLE 8

Preparation of Phosphatidyl-Hydroxyproline from PC 180 ml of acetate buffer, 0.2 M+calcium chloride, 0.04 M, pH 5.6 are placed in a jacketed reactor with a shaker and reflux condenser, after which 112 g of hydroxyproline is added and solubilised by heating to 45° C. The entire process is conducted under nitrogen.

Once solubilisation is complete, 27 g of purified soybean lecithin as per example 2 is added; 10 minutes later, 290 U of phospholipase D as per example 1 is added and it is left to react for 24 hours at 45° C.

Once the reaction is complete, the reactor is unloaded by adding 200 ml of a mixture of n-hexane/isopropanol/water (60/80/15) and the mass is dissolved by shaking, then the shaking is stopped and the two phases are left to separate.

The lower phase is discarded.

The upper phase is washed with 150 ml of 1 N HCl and 30 ml of isopropanol at 5° C.

The acid phase is counter-extracted with 180 ml of a mixture of n-hexane/isopropanol/water (60/80/15), then the two organic phases are washed in a cascade with a mixture of 100 ml water and 130 ml of isopropanol The organic phases are concentrated under vacuum and precipitated by the slow addition of a solution of 8 ml of 4.5 M sodium acetate in water in 600 ml of ethanol.

It is filtered and dried.

This yields 18.4 g of phosphatidyl-hydroxyproline with a titer of over 95%, a phosphatidic acid content of less than 5% and a peroxide index of less than 5.

EXAMPLE 9

Preparation of Phosphatidylglycerol from PC 200 ml of acetate buffer, 0.2 M+calcium chloride, 0.04 M, pH 5.6 are placed in a jacketed reactor with a shaker and reflux condenser. The entire process is conducted under nitrogen.

80 g of glycerol is added; it is heated to 45° C., then 30 g of purified soybean lecithin as per example 2 is added; 10 minutes later, 325 U of phospholipase D as per example 1 is added and it is left to react for 24 hours at 45° C.

Once the reaction is complete, the reactor is unloaded by adding 400 ml of a mixture of n-hexane/isopropanol/water (60/80/15), then the shaking is stopped and the two phases are left to separate.

The lower phase is discarded.

The upper phase is washed with 150 ml of 1 N HCl and 30 ml of isopropanol at 5° C.

The acid phase is counter-extracted with 180 ml of a mixture of n-hexane/isopropanol/water (60/80/15), then the two organic phases are washed in a cascade with a mixture of 100 ml water and 130 ml of isopropanol, then with 100 ml of sodium acetate, 1 N, and 130 ml of isopropanol.

The organic phases are concentrated under vacuum.

Purification is performed by silica gel chromatography using an axial pressure chromatograph with a 1-lt column equilibrated with chloroform/methanol (80/20). Gradient elution is performed till chloroform/methanol/water (70/30/3).

The pure fractions are evaporated, dissolved in 250 ml of cyclohexane and freeze-dried, giving 22.2 g of a white, solid product free from phosphatidic acid and lyso derivatives, with over 95% purity.

This is filtered and dried.

EXAMPLE 10

Harvesting and Recycling of L-Serine

The mother waters from the first partitioning of the enzymatic reaction as per example 2 are kept at a temperature of 0° C. for 24 hours, then the crystallised product is filtered. It is washed with ethanol and dried, giving white needles of pure product identical to the original.

The deficit in quantity (about 20%) is added and the product can be used as normal.

EXAMPLE 11

Examples of Pharmaceutical Compositions (a) Each gelatinous capsule contains:

| | |
|---|---|
| phosphatidylserine | 100.0 mg |
| vegetal oil | 270.0 mg |
| soy lecithin | 30.0 mg |

(b) Each injectable vial contains:

| | |
|---|---|
| phosphatidylserine | 50.0 mg |
| mannitol | 100.0 mg |
| soy lecithin (injectable grade) | 7.5 mg |
| phosphate buffer | 2.2 mg |
| water | q.s.a. 2.0 ml |

EXAMPLE 12

Examples of Food and Dietary Supplements (a) Each gelatinous capsule contains:

| | |
|---|---|
| phosphatidylserine | 100.0 mg |
| vitamin E | 5.0 mg |
| vegetal oil | 295.0 mg |

(b) Each sachet contains:

| | |
|---|---|
| phosphatidylserine | 100.0 mg |
| creatine | 1.5 gr |
| beta-carotene | 0.6 mg |
| vitamin E | 5.0 mg |
| vitamin C | 30.0 mg |
| vitamin B1 | 0.7 mg |
| vitamin B6 | 1.0 mg |
| vitamin B12 | 0.5 mcg |
| folic acid | 0.1 mg |

(c) Each chewable tablet contains:

| | |
|---|---|
| phosphatidylserine | 75.0 mg |
| vitamin E | 5.0 mg |
| vitamin C | 30.0 mg |
| vitamin B1 | 0.7 mg |
| vitamin B6 | 1.0 mg |
| vitamin B12 | 0.5 mcg |
| folic acid | 0.1 mg |

EXAMPLE 13

Examples of Cosmetic Compositions (a) Each Body Cream Tube contains:

| | |
|---|---|
| phosphatidylserine | 4.0 gr |
| macadamia ternifolia | 2.0 gr |
| sodium hyaluronate | 10.0 mg |
| cetearyloctanoate | 8.0 gr |
| caprylic/capric tryglyceride | 7.0 gr |
| sorbitol | 5.0 gr |
| cetearyl alcohol | 4.0 gr |
| polysorbate 20 | 1.0 gr |
| carbomer | 0.8 gr |
| sodium dehydroacetate | 0.4 gr |
| disodium EDTA | 0.3 gr |
| antioxidant (tocopherol) | 50.0 mg |
| water | q.s.a. 100.0 ml |

(b) Each Body Ointment Tube contains:

| | |
|---|---|
| phosphatidylserine | 3.0 gr |
| cholesterol | 2.0 gr |

EXAMPLE 13-continued

Examples of Cosmetic Compositions

| | |
|---|---|
| sodium hyaluronate | 10.0 mg |
| cetearyloctanoate | 9.0 gr |
| caprylic/capric tryglyceride | 7.0 gr |
| sorbitol | 7.0 gr |
| cetearyl alcohol | 3.5 gr |
| polysorbate 20 | 1.0 gr |
| carbomer | 0.6 gr |
| sodium dehydroacetate | 0.5 gr |
| disodium EDTA | 0.3 gr |
| antioxidant (tocopherol) | 50.0 mg |
| water | q.s.a. 100.0 |

What is claimed is:

1. A process for the preparation of phosphatides with the formula (I):

$$R-O-PO(OH)-O-R_1 \quad (I)$$

wherein R is diacylglycerol and $R_1$ is an hydroxl group which process comprises:

reacting a phosphatide of the formula (II):

$$R-O-PO(OH)-O-R_2 \quad (II)$$

wherein R means as above and $R_2$ is $CH_2-CH_2-NH_2$ or $CH_2-CH_2-N(CH_3)_3$, with a primary or secondary alcohol with a chain length of between C2 to C4, optionally substituted with one or more polar groups selected from the group consisting of amino, hydroxy and carboxy, in a single aqueous phase in the presence of an effective amount of phospholipase D with transphosphatidylation activity produced from a *Streptomyces hachijoense* strain to catalyze the reaction to obtain a phosphatide according to formula (I).

2. The process according to claim 1, wherein the diacylglycerol consists of two fatty acids, which may be the same or different, saturated or unsaturated, having a length of between C12 to C24.

3. The process according to claim 1 or 2, wherein the reaction temperature is 45° C.±5° C.

4. The process according to claim 1, wherein the phospholipase D is a purified phospholipase D purified on an anionic cationic exchange resin.

5. The process according to claim 4, wherein the purified phospholipase D used is eluted at pH 6.2 from the cationic exchange resin.

6. The process according to claim 1, wherein the *Streptomyces hachijoense* strain is ATCC 19769.

7. The process according to claim 1, wherein the phosphatide of formula (I) is phosphatidyl-L-serine and the phosphatide of formula (II) is purified soybean lecithin.

8. The process according to claim 1, wherein the phosphatide of formula (I) is phosphatidyl-L-serine and the phosphatide of formula (II) is crude soybean lecithin.

9. The process according to claim 1, wherein the phosphatide of formula (I) is phosphatidyl-L-serine and the phosphatide of formula (II) is egg lecithin.

10. The process according to claim 4, wherein the phosphatide of formula (I) is phosphatidyl-D-serine, phosphatidylethanolamine, phosphatidyl-homoserine, phosphatidyl-hydroxyproline or phosphatidylglycerol.

* * * * *